United States Patent
Komatsu et al.

(10) Patent No.: US 7,932,288 B2
(45) Date of Patent: Apr. 26, 2011

(54) COMPOSITION FOR RELIEVING SUBJECTIVE SYMPTOMS OF FATIGUE

(75) Inventors: Miho Komatsu, Tsukuba (JP); Koji Morishita, Tsukuba (JP); Akemi Ogawa, Matsudo (JP); Goro Hori, Tsuchiura (JP); Miho Takada, Tsuchiura (JP)

(73) Assignee: Kyowa Hakko Bio Co., Ltd., Tokyo (JP)

(*) Notice: Subject to any disclaimer, the term of this patent is extended or adjusted under 35 U.S.C. 154(b) by 289 days.

(21) Appl. No.: 12/089,078

(22) PCT Filed: Oct. 4, 2006

(86) PCT No.: PCT/JP2006/319855
§ 371 (c)(1),
(2), (4) Date: Apr. 3, 2008

(87) PCT Pub. No.: WO2007/040244
PCT Pub. Date: Apr. 12, 2007

(65) Prior Publication Data
US 2009/0232917 A1    Sep. 17, 2009

(30) Foreign Application Priority Data

Oct. 4, 2005 (JP) ................ 2005-290763
Jul. 31, 2006 (JP) ................ 2006-207646

(51) Int. Cl.
*A61K 31/195* (2006.01)
(52) U.S. Cl. ...................... 514/564; 562/561
(58) Field of Classification Search .............. None
See application file for complete search history.

(56) References Cited

U.S. PATENT DOCUMENTS

2006/0211721 A1 * 9/2006 Roberts ............... 514/276

FOREIGN PATENT DOCUMENTS

| CN | 1125100 A | * | 6/1996 |
| DE | 2150900 | | 4/1972 |
| FR | 2110465 A1 | | 6/1972 |
| GB | 1310658 | | 3/1973 |
| JP | 38-24890 B1 | | 11/1963 |
| JP | 41-8592 A | | 5/1966 |
| JP | 42007767 | | 3/1967 |
| JP | 46003194 | | 1/1971 |
| JP | 1-291761 A | | 11/1989 |
| JP | 2003-116494 A | | 4/2003 |

OTHER PUBLICATIONS http://thesaurus.reference.com/browse/fatigue—accessed Feb. 2010.*
Cutinelli, L. et al. "Protection by Ornithine-Aspartate of the Effects of Physical Exercise" Arzneimittel-Forschung, 1970, vol. 20, No. 8, pp. 1064-1067.
Shibasaki, T. et al. "L-Ornithine and Fatigue Recovery." Food Style 21, 2006, vol. 10, No. 1, pp. 13-15. (Relevance satisfied by attached Search Report).

* cited by examiner

*Primary Examiner* — Susan C Hoffman
(74) *Attorney, Agent, or Firm* — Leydig, Voit & Mayer, Ltd.

(57) ABSTRACT

There has been a demand in the marketplace for medicines, functional foods and so on which can relieve subjective symptoms of fatigue in persons having these subjective symptoms, and enabling the persons to have productive days. That is, an object of the present invention is to provide a composition for relieving subjective symptoms of fatigue. According to the present invention, a safe and effective composition for relieving subjective symptoms of fatigue which contains ornithine or a salt thereof as an active ingredient can be provided.

6 Claims, 4 Drawing Sheets

FIG. 1

Q1  Feel heavy in the head

Do not feel                                    Always feel heavy in the head
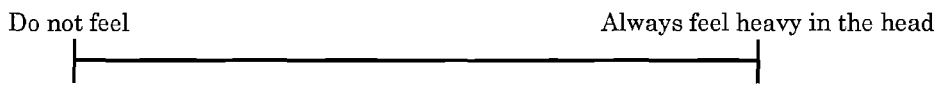

Q2  Feel tired in the whole body

Do not feel       Always feel tired as if the whole body were cotton impregnated with water
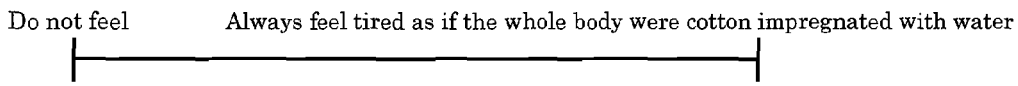

Q3  Feel tired in the legs

Do not feel       Always feel tired in the legs such that one wants a strong masage
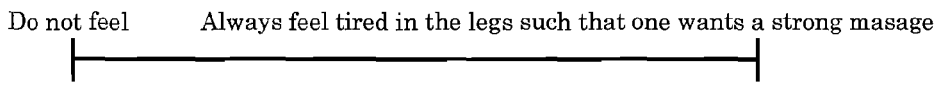

Q4  Give a yawn

Do not give a yawn                             Give a yawn if not careful
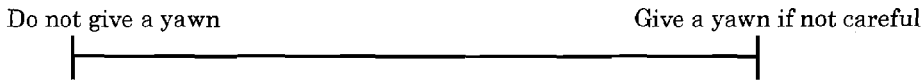

Q5  Feel the brain muddled

Do not feel                                    Always feel the brain muddled
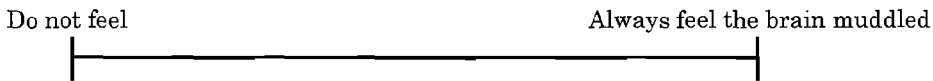

Q6  Feel drowsy

Do not feel                                    Always feel drowsy
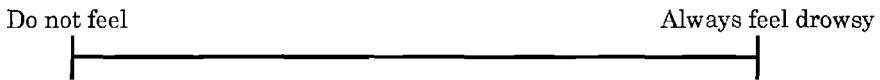

Q7  Feel strained in the eyes

Do not feel                                    Always feel strained in the eyes
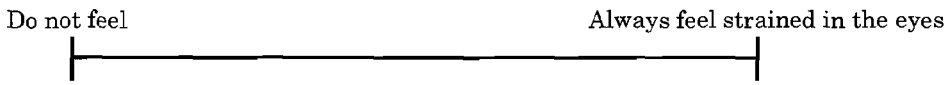

Q8  Feel pain in standing in daily life

Do not feel           Feel much pain in standing if not sitting on something
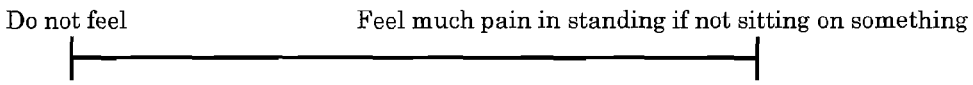

FIG. 2
Q9 Feel difficult in thinking
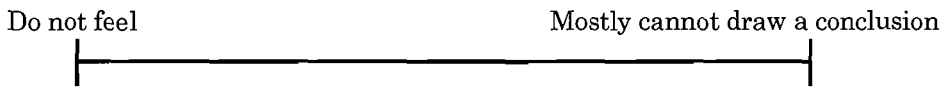
Q10 Become weary of talking
Q11 Feel irritated
Q12 Unable to concentrate attention
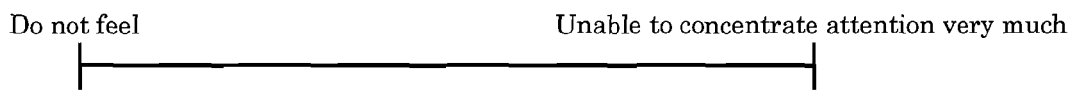
Q13 Unable to have an interest in things
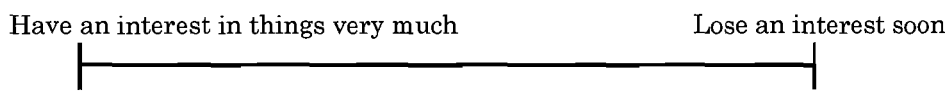
Q14 Apt to forget things
Q15 Apt to make mistakes

COMPOSITION FOR RELIEVING SUBJECTIVE SYMPTOMS OF FATIGUE

CROSS REFERENCE TO PRIOR APPLICATION

This is a U.S. National Phase Application under 35 U.S.C. §371 of International Patent Application No. PCT/JP2006/319855 filed Oct. 4, 2006, which claims the benefit of Japanese Patent Application Nos. 2005-290763 filed Oct. 4, 2005 and 2006-207646 filed Jul. 31, 2006, all of which are incorporated by reference herein. The International Application was published in Japanese on Apr. 12, 2007 as WO 2007/040244 A1 under PCT Article 21(2).

TECHNICAL FIELD

The present invention relates to a composition for relieving subjective symptoms of fatigue comprising ornithine or a salt thereof as an active ingredient.

BACKGROUND ART

In fatigue, pathological fatigue and physiological fatigue are known, and it is said that the pathological fatigue which is observed while being ill or performing excessive exercise is associated with an increase in the blood ammonia level. On the other hand, in physiological fatigue in normal subjects, an increase in the blood ammonia level is not observed.

Further, as the method for assessing feelings of fatigue, i.e., subjective symptoms of fatigue, a method using the table for assessing subjective symptoms (Non-patent document 1) made by the Industrial Fatigue Research Committee belonging to the Japan Society for Occupational Health is known. According to the table for assessing subjective symptoms, feelings of fatigue are classified into three factors, which are considered as follows: "drowsiness and dullness" (Group 1), "difficulty in concentration" (Group 2), and "physical discomfort" (Group 3).

Ornithine is used, mostly in the U.S. and Japan, as a food material to strengthen muscle formation through secretion of growth hormone or to prevent obesity by enhancing basal metabolism. Further, ornithine is used in the form of L-ornithine-L-aspartate as a medicament used to improve a liver disorder in Europe.

It is known that in pathological fatigue associated with an increase in the blood ammonia level, by administering ornithine or a salt thereof, the blood ammonia level is lowered thereby to relive the pathological fatigue (Patent documents 1 to 3 and Non-patent document 2). However, it is not known that feelings of fatigue, i.e., subjective symptoms of fatigue in physiological fatigue in normal subjects are relieved by ornithine or a salt thereof.

Patent document 1: Japanese Published Examined Patent Application No. 7767/1967
Patent document 2: Japanese Published Examined Patent Application No. 3194/1971
Patent document 3: Japanese Published Examined Patent Application No. 8592/1966
Non-patent document 1: Hirou no Sokutei to Hyoka (Determination and Evaluation of Fatigue)
Non-patent document 2: "Arzneim.-Forsch (Drug Res.)", Vol. 8, pp. 1064-1067, 1970

DISCLOSURE OF THE INVENTION

Problems to be Solved by the Invention

There has been a demand in the marketplace for medicaments, functional foods and so on which can relieve subjective symptoms of fatigue in persons having these subjective symptoms, enabling the persons to have productive days. That is, an object of the present invention is to provide a composition for relieving subjective symptoms of fatigue.

Means for Solving the Problems

The present invention relates to the following (1) to (12).
(1) A composition for relieving subjective symptoms of fatigue, which comprises ornithine or a salt thereof as an active ingredient.
(2) The composition according to the above (1), wherein the subjective symptoms of fatigue are subjective symptoms of physiological fatigue.
(3) The composition according to the above (1) or (2), wherein the subjective symptoms of fatigue are symptoms related to drowsiness and dullness or difficulty in concentration.
(4) The composition according to any one of the above (1) to (3), which further comprises garlic or a garlic extract.
(5) A method of relieving subjective symptoms of fatigue, which comprises administering to a subject in need thereof, or allowing the subject to ingest, an effective amount of ornithine or a salt thereof.
(6) The method according to the above (5), wherein the subjective symptoms of fatigue are subjective symptoms of physiological fatigue.
(7) The method according to the above (5) or (6), wherein the subjective symptoms of fatigue are symptoms related to drowsiness and dullness or difficulty in concentration.
(8) The method according to any one of the above (5) to (7), which further comprises administering garlic or a garlic extract or having garlic or a garlic extract ingested.
(9) Use of ornithine or a salt thereof for the manufacture of a composition for relieving subjective symptoms of fatigue.
(10) The use according to the above (9), wherein the subjective symptoms of fatigue are subjective symptoms of physiological fatigue.
(11) The use according to the above (9) or (10), wherein the subjective symptoms of fatigue are symptoms related to drowsiness and dullness or difficulty in concentration.
(12) The use according to any one of the above (9) to (11), which further comprises use of garlic or a garlic extract.

EFFECT OF THE INVENTION

According to the present invention, a safe and effective composition for relieving subjective symptoms of fatigue which comprises ornithine or a salt thereof as an active ingredient can be provided.

BRIEF DESCRIPTION OF THE DRAWINGS

FIG. 1 is scale graphs expressing questionnaires for evaluation using Visual Analogue Scale (VAS) method. Each end of the segment has a criterion of expression.

FIG. 2 is scale graphs expressing questionnaires for evaluation using Visual Analogue Scale (VAS) method. Each end of the segment has a criterion of expression.

BEST MODE FOR CARRYING OUT THE INVENTION

Figure 3:
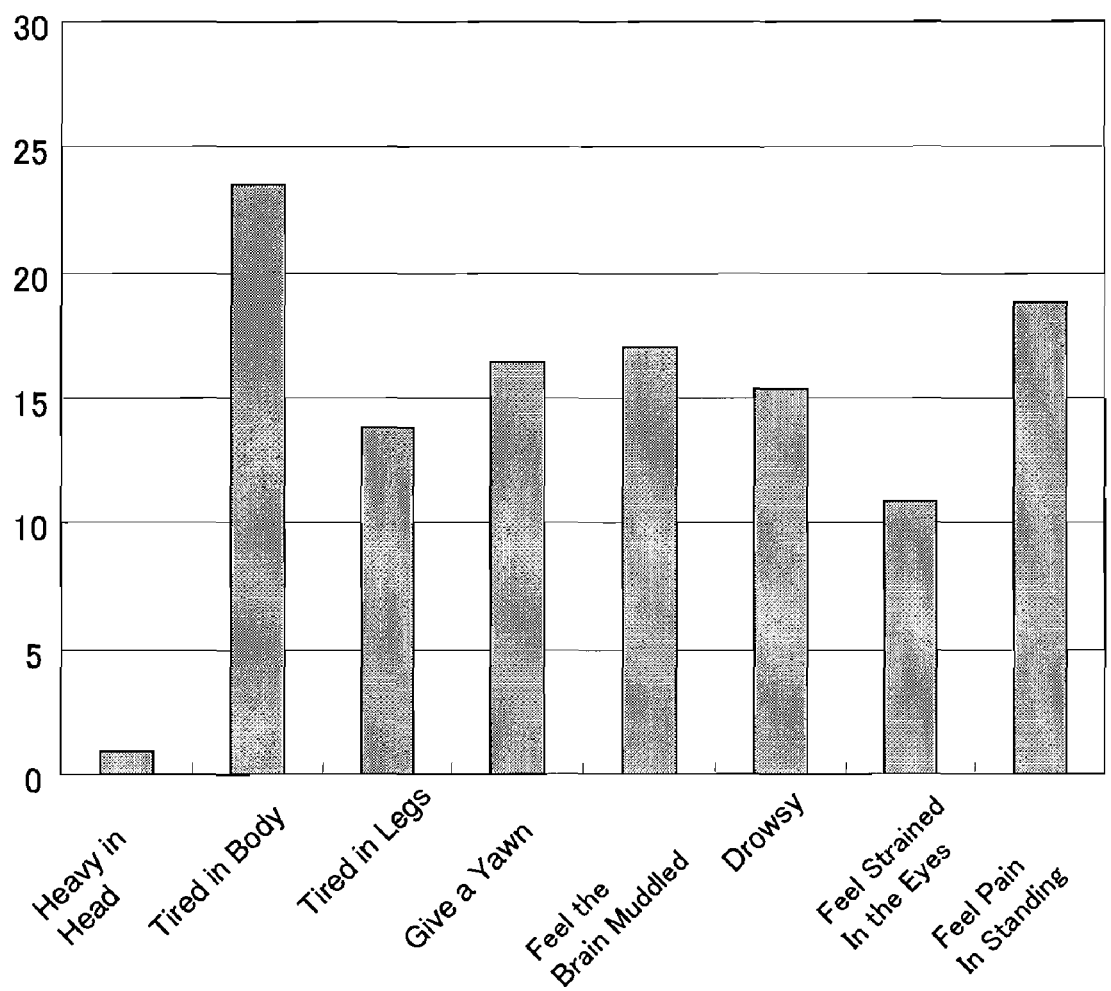
FIG. 3 is a graph showing improvements by ingestion of ornithine in relieving subjective symptoms of fatigue. The vertical axis shows an average improvement ratio (%) of each criterion related to drowsiness and dullness.

Ornithine as applied in the present invention includes L-ornithine and D-ornithine, preferably L-ornithine. Ornithine can be obtained by a chemical synthetic method or a fermentation method. Also, ornithine can be commercially available. The chemical synthetic method can be found in, for example, Coll. Czechoslov. Chem. Commun., 24, 1993 (1959). The fermentation method for ornithine is disclosed in, for example, Japanese Published Unexamined Patent Application Nos. 24096/78 and 119194/86. L-Ornithine and D-ornithine can be also purchased from, for example, Sigma Aldrich Company.

Salts of ornithine include acid addition salts, metal salts, ammonium salts, organic amine addition salts, amino acid addition salts and the like. The acid addition salts include inorganic acid salts such as hydrochloride, hydrosulfate, nitrate and phosphate; and organic acid salts such as acetate, maleate, fumarate, citrate, malate, lactate, α-ketoglutarate, gluconate and caprylate. The metal salts include alkali metal salts such as sodium salt and potassium salt; alkaline earth metal salts such as magnesium salt and calcium salt; aluminum salt, zinc salt and the like.

Ammonium salts include salts of ammonium, tetramethylammonium and the like. Organic amine addition salts include salts of morpholine, piperidine and the like. Amino acid addition salts include salts of glycine phenylalanine, lysine, aspartate, glutamate and the like.

Among the above salts, hydrochloride, citrate, malate, α-ketoglutarate and aspartate are preferably applied, but one of the remaining salts or two or more in combination, of the above salts can be arbitrarily used.

In the composition of the present invention, in addition to the incorporation of ornithine or a salt thereof as an active ingredient, further garlic (Allium sativum L.) or a garlic extract may be incorporated. Such garlic or a garlic extract to be used in the present invention may be in any form as long as it contains alliin or a degradation product thereof called allicin known as a component effective in relieving fatigue. The garlic extract can also be purchased from, for example, Bizen Chemical Co. Ltd. or the like.

In the case where garlic or a garlic extract is incorporated in the composition of the present invention, the compounding ratio of ornithine or a salt thereof to alliin or allicin is from 1:10000 to 10000:1, preferably from 1:3000 to 3000:1, particularly preferably from 1000:1 to 1:1000 in terms of dry weight ratio.

In the composition of the present invention, in addition to ornithine or a salt thereof, an additive suitable for each application can be properly incorporated.

Examples of the additive include amino acids such as valine, leucine, isoleucine, arginine, lysine, glutamine, alanine, serine, glycine, cysteine and threonine.

The composition of the present invention can be used as a medicament or a food additive (hereinafter, also referred to as the medicament or food additive of the present invention).

In the case where the composition of the present invention is used as a medicament, ornithine or a salt thereof can be administered as such, and however, usually it is desirable that they are provided as any of various kinds of pharmaceutical preparations.

The pharmaceutical preparation contains ornithine or a salt thereof as the active ingredient, and however, it may contain any other active ingredients for the therapy. Further, these pharmaceutical preparations may be produced by any method well known in the technical field of pharmaceutics by mixing the active ingredients with one or more pharmaceutically acceptable carriers.

With regard to the route of administration of the pharmaceutical preparation, it is desirable to select a route of administration that is the most effective for the therapy, and examples thereof include oral administration and parenteral administration such as intravenous administration, intraperitoneal administration or subcutaneous administration, and oral administration is preferred.

With regard to the dosage form, any of oral preparations such as tablets, powders, granules, pills, suspensions, emulsions, infusions, decoctions, capsules, syrups, liquid preparations, elixirs, extracts, tinctures and fluid extracts and parenteral preparations such as injections, drippings, creams and suppositories may be used, and oral preparations are preferably used.

A liquid preparation such as a syrup, which is suitable for oral administration, can be formulated by adding water, a saccharide such as sucrose, sorbitol or fructose, a glycol such as polyethylene glycol or propylene glycol, an oil such as sesame oil, olive oil or soybean oil, an antiseptic such as a p-hydroxybenzoate ester, a preservative such as a p-oxybenzoate derivative (e.g., methyl paraoxybenzoate) or sodium benzoate, a flavor such as strawberry flavor or peppermint, or the like.

Further, for example, tablets, powders or granules, each of which is suitable for oral administration, can be prepared by adding a saccharide such as lactose, sugar, glucose, sucrose, mannitol or sorbitol, starch such as that of potato, wheat or corn, an inorganic substance such as calcium carbonate, calcium sulfate, sodium hydrogen carbonate or sodium chloride, an excipient such as crystalline cellulose or plant powder (e.g., licorice root powder, gentian powder or the like), a disintegrator such as starch, agar, gelatin powder, crystalline cellulose, carmellose sodium, carmellose calcium, calcium carbonate, sodium hydrogen carbonate or sodium alginate, a lubricant such as magnesium stearate, talc, hydrogenated plant oil, macrogol or silicone oil, a binder such as polyvinyl alcohol, hydroxypropyl cellulose, methyl cellulose, ethyl cellulose, carmellose, gelatin or starch paste, a surfactant such as a fatty acid ester, a plasticizer such as glycerol, or the like.

For example, an injection, which is suitable for parenteral administration, preferably comprises a sterilized aqueous preparation containing ornithine or a salt thereof, which is isotonic to the recipient's blood. In the case of an injection, for example, a solution for injection is prepared using a carrier comprising a salt solution, a glucose solution, or a mixture of a salt solution and a glucose solution, or the like.

Further, also in these parenteral preparations, one or more auxiliary components selected from the antiseptics, preservatives, flavors, excipients, disintegrators, lubricants, binders, surfactants and plasticizers described in the examples of the oral preparations, and the like.

The concentration of ornithine or a salt thereof, in the pharmaceutical composition of the present invention is appropriately selected depending on the type of preparation, the effect expected by administration of the preparation, and the like, and however, the concentration in terms of ornithine a salt thereof, is usually 0.1 to 100% by weight, preferably, 0.5 to 80% by weight, particularly preferably 1 to 70% by weight.

The dose and the administration frequency of the pharmaceutical composition of the present invention may vary depending on the administration form, the age and the body weight of the patient, and the nature or the severity of the symptom to be treated. In general, it is administered once to several times a day in an amount of usually 50 mg to 30 g, preferably 100 mg to 10 g, more preferably 200 mg to 3 g per day for an adult in terms of ornithine or a salt thereof.

The administration period is not particularly limited, and however, it is usually one day to one year, preferably, one week to three months.

In the case where the composition of the present invention is used as a food additive, ornithine or a salt thereof can be used as such, and however, the food additive comprising ornithine or a salt thereof as the active ingredient may be prepared according to the same method as in the above pharmaceutical preparations.

The food additive of the present invention can be processed and produced in a form of powder, granules, pellets, tablets and various kinds of liquid preparations by, if necessary, mixing or dissolving other food additives therein.

A food or drink containing the food additive of the present invention (hereinafter referred to as the food or drink of the present invention) can be processed and produced by a common production process for foods or drinks except that the food additive of the present invention is added to the food or drink.

The food or drink of the present invention can also be produced by a granulation method such as fluid bed granulation, stirring granulation, extrusion granulation, oscillating granulation, gas stream granulation, compression molding granulation, disruption granulation, spray granulation or jet granulation; a coating method such as pan coating, fluid bed coating or dry coating; a swelling method such as puff drying, an excess steam method, a foam mat method or a microwave heating method; an extrusion method such as using an extruding granulator or an extruder; or the like.

The food or drink of the present invention may be in any forms such as juice, soft drinks, tea, lactic acid bacteria beverage, milk products such as fermented milk, ice cream, butter, cheese, yogurt, processed milk and skim milk, meat products such as ham, sausage and hamburger, fish paste foods such as kamaboko (boiled fish paste), chikuwa (a kind of Japanese fish sausage) and satsuma-age (deep-fried fish ball containing vegetable bits), egg products such as dashimaki (omelet with stock) and tamago-dofu (steamed beaten egg with soup stock), confectionary such as cookies, jelly, chewing gum, candy and snacks, bread, noodles, pickles, smoked fish and meat, dried fish, tsukudani (simmered meat in soy sauce and sugar), salted products, soup, seasonings, and the like.

The food or drink of the present invention may also be in a form such as a powdered food, a sheet-shaped food, a bottled food, a canned food, a retort food, a capsule food, a tablet food, a liquid food or a drinkable preparation.

The food or drink of the present invention can be used as a food or drink such as a health food, a functional food, a nutritional supplement or a food for a specific health use for relieving subjective symptoms of fatigue.

To the food or drink or the food additive of the present invention, an additive generally used in foods or drinks, for example, a sweetener, a coloring agent, a preservative, a thickening stabilizer, an antioxidant, a color-developing agent, a bleaching agent, an anti-fungal agent, a gum base, a bitter agent, an enzyme, a wax, a sour agent, a seasoning, an emulsifier, a nutrient supplement, an additional material for preparation, a flavor, a spice extract or the like described in Japan's Specifications And Standards For Food Additives (Japan Food Additives Association, issued on Jan. 6, 1997) may be added.

The amount of the food additive to be incorporated into the food or drink of the present invention is appropriately selected depending on the type of food or drink, the effect expected by ingestion of the food or drink, and the like, and however, in terms of ornithine or a salt thereof, it is usually added thereto in an amount of 0.1 to 90% by weight, preferably, 0.5 to 80% by weight, particularly preferably 1 to 70% by weight.

The ingestion amount of the food or drink of the present invention may vary depending on the ingestion form, the age and the body weight of the ingesting person, and the like. In general, it is ingested once to several times a day in an amount of usually 50 mg to 30 g, preferably 100 mg to 10 g, more preferably 200 mg to 3 g per day for an adult in terms of the ornithine or a salt thereof.

The ingestion period is not particularly limited, and however, it is usually one day to one year, preferably, one week to three months.

By the administration or ingestion of the medicament or food or drink of the present invention, subjective symptoms of fatigue can be relieved.

The subjective symptoms of fatigue as used herein have the same definitions as feelings of fatigue.

As fatigue, physiological fatigue and pathological fatigue can be exemplified, and however, the medicament or food or drink of the present invention is preferably used for relieving subjective symptoms of physiological fatigue.

The physiological fatigue means a protective response to maintain good health in humans. More specifically, it means fatigue caused by a daily activity such as paid work, housework or a sport during leisure time, and includes not only physical fatigue but also mental fatigue.

On the other hand, pathological fatigue means fatigue occurring as a symptom accompanying pre-existing diseases such as heart diseases, bronchial asthma, hepatitis, anemia, metabolic diseases, muscle diseases, various infectious disease and cancer, and fatigue involved in chronic fatigue syndrome, depression due to mental causes, overtraining syndrome due to sport and the like.

The subjective symptoms of fatigue which can be relived by the administration or ingestion of the medicament or food or drink of the present invention are not particularly limited, and however, symptoms related to drowsiness and dullness, and difficulty in concentration can be preferably exemplified.

As the symptoms related to drowsiness and dullness, for example, feel heavy in the head, feel tired in the whole body, feel tired in the legs, give a yawn, feel the brain muddled, feel drowsy, feel strained in the eyes, feel pain in standing, and the like can be exemplified.

As the symptoms related to difficulty in concentration, for example, feel difficult in thinking, become weary of talking, feel irritable, unable to concentrate attention, unable to have an interest in things, become apt to forget things, apt to make mistakes, and the like can be exemplified.

Hereinafter, the test examples in which the effect of ornithine on relieving subjective symptoms of fatigue was studied will be described.

TEST EXAMPLE 1

A test was carried out as follows. Fourteen normal subjects of each male and female at the age of 45 to 64 were divided into two groups each consisting of 7 subjects and allowed to ingest 6 tablets of Example 1 (the tablet containing ornithine) or 6 tablets of Comparative example 1 (the tablet not containing ornithine) per day for 3 weeks. Evaluation was carried out in terms of the subjective symptoms of fatigue in the test subjects at the start and completion of the test using a visual analogue scale (VAS) method.

Specifically, each end of the segment has a criterion of expression. Referring to FIG. 1 or 2, each subject was allowed to mark somewhere in the segment, corresponding to each term of the questionnaires. Among the subjective symptoms of fatigue, questionnaires 1 to 8 represent indices related to "drowsiness and dullness", and questionnaires 9 to 15 represent indices related to "difficulty in concentration".

The distance (mm) from the left end of the segment to the marked point was measured and the difference between before and after the test was calculated. The difference by the value before the test was shown in the percentage calculated; and the average value and standard deviation for each group were calculated. Further the average relief ratio (%) was determined to be a value obtained by subtracting the average value of the placebo group from the average value of the ornithine group. Further, it was confirmed that there was no difference between two groups at the start of the test.

Further, at the start and completion of the test, the blood ammonia level was measured in 7 test subjects to confirm that the blood ammonia level of each test subject was not changed and fell within the normal range.

Further, the test was carried out under a random assignment and the comparison between the double blind parallel groups was carried out. The study of statistically significant difference between two groups was carried out by an unpaired t-test of both side distributions using the difference between the start and completion of the test.

Figure 4:
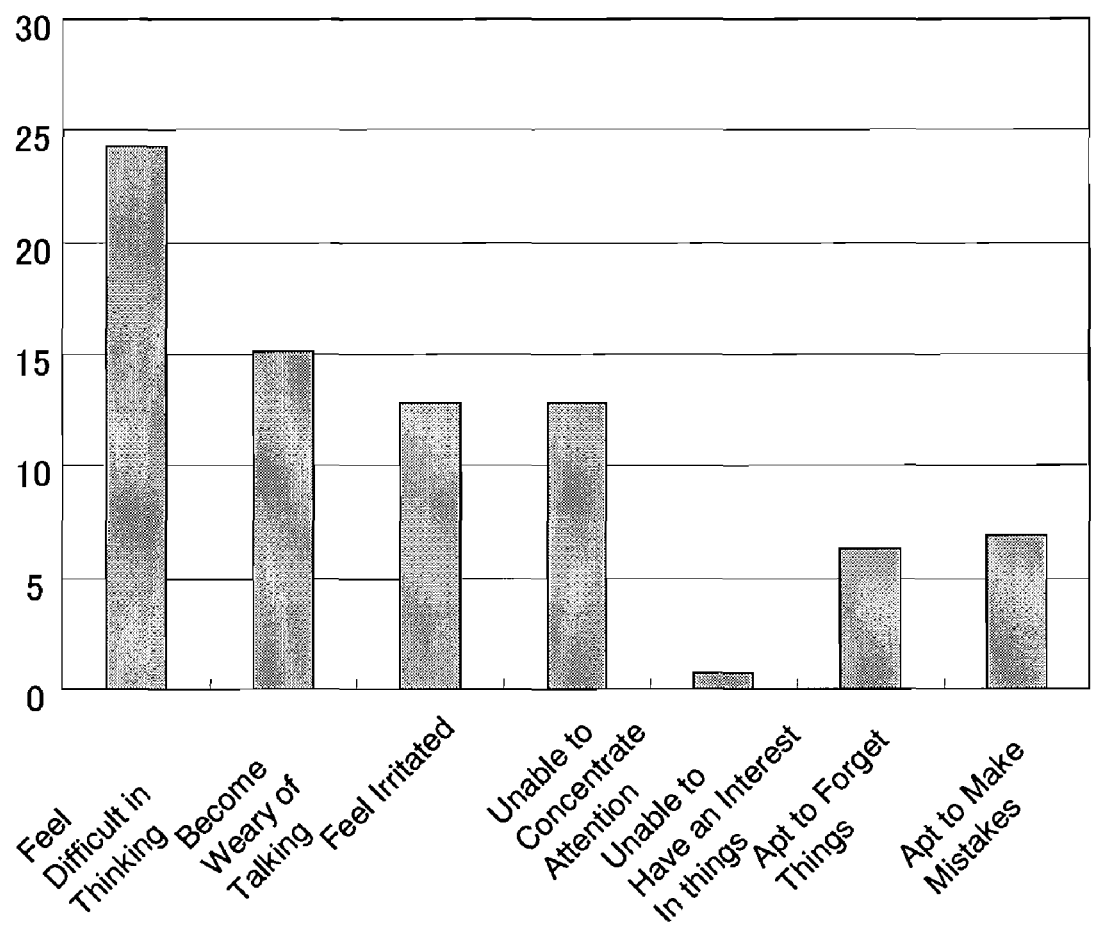
FIG. 4 is a graph showing improvements by ingest of ornithine in relieving subjective symptoms of fatigue. The vertical axis shows average improvements ratio (%) of each criterion related to difficulty in concentration.

The results related to "drowsiness and dullness" are shown in FIG. 3, and the results related to "difficulty in concentration" are shown in FIG. 4. With regard to all the terms, a relieving effect of ingestion of ornithine was shown, and particularly, with regard to "having difficulty thinking", a significant difference between the placebo group and the ornithine group was obtained.

The above results have revealed the effect of ingestion of ornithine on relieving subjective symptoms of fatigue.

TEST EXAMPLE 2

A test was carried out as follows. Twenty-seven normal subjects of each male and female at the age of 20 to 60 were divided into four groups each consisting of 6 to 7 subjects and allowed to ingest 4 capsules shown in Table 1 per day for 1 week.

TABLE 1

|  | Test group | | | |
| --- | --- | --- | --- | --- |
|  | Placebo group (mg/capsule) | Ornithine group (mg/capsule) | Garlic group (mg/capsule) | Ornithine + Garlic group (mg/capsule) |
| Ornithine hydrochloride (available from Kyowa Hakko Kogyo Co., Ltd.) | — | 200 | — | 100 |
| Odorless garlic extract (available from Bizen Chemical Co. Ltd.) | — | — | 100 | 50 |

* As the capsule, a white cellulose hard capsule No. 0 was used, and crystalline cellulose was filled in spaces.
* In the odorless garlic extract, about 1% by dry weight of alliin or allicin is contained.

Evaluation was carried out in terms of the subjective symptoms of fatigue in test subjects at the start and completion of the test in the same manner as in Test example 1.

As a result, with regard to "feel irritable" in "difficulty in concentration", the average relief ratio in the ornithine group was 7.2 and it was 5.1 in the garlic group, and however, it was 9.6 in the ornithine+garlic group, and thus, by a combination of ornithine and garlic, a significant relieving effect was obtained.

Further, with regard to "unable to concentrate attention" in "difficulty in concentration", the average relief ratio in the ornithine group was 3.4 and it was 4.2 in the garlic group, and however, it was 21.2 in the ornithine+garlic group, and thus, by a combination of ornithine and garlic, a significant relieving effect was obtained.

Hereinafter, the examples of the present invention will be described.

EXAMPLE 1

Production of a Tablet Containing Ornithine

A mixture of 136.2 Kg of ornithine hydrochloride (Commercial name: L-ornithine hydrochloride, Kyowa Hakko Co., Ltd.), 36.0 Kg of a fine cellulose crystal (Commercial name: Avcel FD101, Asahi Kaei Chemicals Co., Ltd.); 6.6 kg of sucrose fatty acid ester (Commercial name: DK ester F-20W, Daiichi Kogyo Seiyaku Co., Ltd.); 1.2 kg of calcium phosphate (Commercial name: Tricalcium phosphate, Taihei Chemical Industrial Co., Ltd.); and 20.0 kg of β-cyclodextrin (Commercial name: Seldex B-100, Nihon Shokuhinkako Co., Ltd.) was mixed using a conical blender (CB-1220 Blender, Nihon Kansoki C., Ltd.). The mixture obtained was compressed and molded to a tablet of 250 mg with 8 mm of diameter under 10 KN of compression-molding pressure using the rotary compression molding machine (VIRGO0524SS1AY, Kikusui Seisakusho Co., Ltd.).

EXAMPLE 2

Production of an Enteric Capsule Containing Ornithine

A mixture of 20 kg of the mixture produced in Example 1 and 0.2 kg of silicon dioxide was mixed and stirred. The mixture obtained was put into a capsule-filling machine to fill 20,000 tablets of gelatin Number 2 hard-capsules to provide the hard-capsules. The surfaces of the hard-capsules obtained were coated with a zein solution using High Coater HCT-48 (Freund Corporation) to produce 20,000 enteric capsules containing ornithine hydrochloride.

EXAMPLE 3

Production of an Enteric Tablet Containing Ornithine

The surfaces of the tablets produced in Example 1 were coated with shellac solution using High Coater HCT-48 (Freund Corporation) to produce an enteric tablet.

EXAMPLE 4

Production of a Drink Containing Ornithine

Each 1.28 kg of ornithine hydrochloride (Commercial name: L-ornithine hydrochloride, Kyowa Hakko Kogyo Co., Ltd.); 3 kg of erythritol (Nikken Kagaku Co., Ltd.); 0.05 kg of citric acid (Kyowa Hi Foods Co., Ltd.); 3 g of artificial sweetener; and 0.06 g of flavor were stirred and dissolved in 50 L of water at solution temperature 70° C. After the pH of the solution was adjusted to 3.3, the solution was sterilized using plate sterilization and filled into bottles. The bottle was sterilized using a pasteurizer to produce a drink.

EXAMPLE 5

Production of a Drink Containing Ornithine and a Garlic Extract 0.64 Kg of ornithine hydrochloride, 0.6 Kg of an odorless garlic extract, 3 Kg of erythritol, 0.05 Kg of citric acid, 3 g of an artificial sweetener, and 0.06 Kg of a flavor were stirred and dissolved in 50 L of water at a solution temperature of 70° C. After the pH of the solution was adjusted to 3.3, the solution was sterilized using plate sterilization and filled into a bottle. The bottle was sterilized using a pasteurizer to produce a drink.

COMPARATIVE EXAMPLE 1

Instead of ornithine hydrochloride in Example 1, the same amount of lactose was used to produce a tablet not containing ornithine.

INDUSTRIAL APPLICABILITY

According to the present invention, a safe and effective composition for relieving subjective symptoms of fatigue which contains ornithine or a salt thereof as an active ingredient can be provided.

The invention claimed is:

1. A method for relieving one or more symptoms of physiological fatigue, which comprises administering to a subject in need thereof, an effective amount of ornithine or a salt thereof, thereby relieving one or more symptoms of physiological fatigue.

2. The method according to claim 1, wherein the one or more symptoms of physiological fatigue are one or more symptoms related to drowsiness, dullness, or difficulty in concentration.

3. The method according to claim 2, which further comprises administering or ingesting garlic or a garlic extract.

4. The method according to claim 3, wherein the one or more symptoms of physiological fatigue are one or more symptoms related to difficulty in concentration.

5. The method according to claim 2, wherein the one or more symptoms of physiological fatigue are one or more symptoms related to difficulty in concentration.

6. The method according to claim 1, which further comprises administering or ingesting garlic or a garlic extract.

* * * * *